United States Patent [19]

Suzuki

[11] 4,029,710

[45] June 14, 1977

[54] 4-ALKOXY-N-BUTYRALDEHYDE PREPARATION

[75] Inventor: Shigeto Suzuki, San Francisco, Calif.

[73] Assignee: Chevron Research Company, San Francisco, Calif.

[22] Filed: Mar. 31, 1976

[21] Appl. No.: 672,363

[52] U.S. Cl. .............................. 260/602; 260/615 R
[51] Int. Cl.$^2$ ......................................... C07C 47/02
[58] Field of Search ..................................... 260/602

[56] References Cited

UNITED STATES PATENTS

| 2,288,211 | 6/1942 | Schulz ............................... 260/602 |
| 2,967,890 | 1/1961 | Mercorney ......................... 260/611 |
| 3,519,691 | 7/1970 | von Porletius ..................... 260/602 |

OTHER PUBLICATIONS

Kirt Othmer "Enc. Chem. Tech.", vol. 1, sec. ed. (1963), p. 644.

Primary Examiner—James O. Thomas, Jr.
Assistant Examiner—W. B. Lone
Attorney, Agent, or Firm—D. A. Newell; John Stoner, Jr.; W. Keith Turner

[57] ABSTRACT

A process for preparing 4-alkoxy-n-butyraldehydes which comprises contacting allyl alcohol with formaldehyde and an alcohol in the presence of hydrogen fluoride at a temperature in the range from about −100° to about 10° C.

11 Claims, No Drawings

4-ALKOXY-N-BUTYRALDEHYDE PREPARATION

BACKGROUND OF THE INVENTION

The present invention relates to the production of 4-alkoxy-n-butyraldehydes by the hydrogen fluoride-catalyzed reaction of allyl alcohol, formaldehyde and an alcohol.

4-alkoxy-n-butyraldehyde has various uses as an intermediate in the production of organic compounds. For example, 4-alkoxy-n-butyraldehydes may be hydrogenated to prepare 4-alkoxy-1-butanol, which is an organic solvent. It is known to produce butyraldehydes from unsaturated alcohols by the "oxo synthesis". The oxo synthesis comprises contacting an olefin with carbon monoxide and hydrogen in the presence of a cobalt salt at elevated temperatures and pressures. In general, the oxo synthesis proceeds as follows:

$$RCH_2CH=CH_2 + CO + H_2 \rightarrow RCH_2CH_2CH_2CHO$$

My pending application entitled "Alkoxyacetic Acid or Ester Preparation", Ser. No. 532,563, filed Dec. 13, 1974, now U.S. Pat. No. 3,948,977 discloses a process for producing alkoxyacetic acid from formaldehyde, carbon monoxide and an alcohol.

My pending application entitled "4-Hydroxy-n-Butyraldehyde from Allyl Alcohol and Formaldehyde" discloses a process for producing 4-hydroxy-n-butyraldehyde by contacting formaldehyde and allyl alcohol in the presence of hydrogen fluoride.

SUMMARY OF THE INVENTION

It has now been discovered that 4-alkoxy-n-butyraldehyde can be prepared by contacting allyl alcohol with formaldehyde and an alcohol in the presence of hydrogen fluoride at a temperature of from about −100° to about 10° C and a pressure of from about 10 to about 1000 psia.

DETAILED DESCRIPTION OF THE INVENTION

The present invention is based on the discovery that in the presence of hydrogen fluoride and an alcohol, formaldehyde and allyl alcohol will react to produce an alkoxy aldehyde. Moderate reaction conditions are employed to obtain the alkoxy-substituted product.

The alcohol used to produce alkoxy-n-butyraldehyde in the present process is preferably a $C_1$ to $C_{20}$ primary alcohol or mixture thereof, more preferably a $C_1$ to $C_{10}$ primary alcohol or mixture thereof, and most preferably the alcohol is methanol, ethanol, propanol, n-butanol, or a mixture of any or all of these $C_1$ to $C_4$ alcohols. Saturated alcohols are preferred, although mono-, di- or polyunsaturated alcohols may be employed.

In accordance with the process of the invention, the reaction is carried out in the liquid phase at a temperature of from about −100° to about 10° C, preferably −70° to about −10° C, and a pressure of from about 10 to about 1000 psia, preferably about 1 atmosphere pressure.

Among other factors, the use of a hydrogen fluoride catalyst is believed responsible for the relatively rapid and high conversions obtained under moderate reaction conditions. Hydrogen fluoride is also a solvent for the reaction, and is used in excess of catalytic amounts. Satisfactory conversions on the order of about 95% have been obtained in as little as about 30 minutes using an HF to reactant weight ratio of from about 1:1 to about 10:1, preferably from about 2:1 to about 4:1.

Hydrogen fluoride, per se, is, of course, a suitable catalyst for use in the present process. However, in practice, noninterferring amounts of various diluents and contaminants may be present in the catalyst composition. Thus, suitable hydrogen fluoride catalysts comprise hydrogen fluoride, but may also comprise inert components such as water and dichloromethane.

In addition to superior activity as a catalyst in the present process, hydrogen fluoride is relatively easy to separate from the reaction zone effluent. The boiling point of HF is 19.7° C at one atmosphere pressure, which is considerably more volatile than 4-alkoxy-n-butyraldehydes. Thus, HF is readily separated by distillation and may be recycled to the reaction zone. Some unreacted formaldehyde may be co-distilled with HF and recycled to the reaction zone.

The molar ratio of allyl alcohol to formaldehyde to alcohol will vary, depending upon reaction conditions. However, for general guidance, acceptable molar ratios will range from about 1:1:1 to about 1:10:10, preferably from about 1:2:4 to about 1:406.

The crude reaction product comprising a 4-alkoxy-n-butyraldehyde may be purified in any of several ways. For example, hydrogen fluoride and unreacted formaldehyde and alcohol may be removed by distillation under reduced pressure to leave 4-alkoxy-n-butyraldehyde as a bottoms product. Hydrogen fluoride and formaldehyde may be removed by distillation, and the butyraldehyde separated from the alcohol as a bisulfite addition compound which is readily decomposed into the original aldehyde by contact with aqueous acid.

The following example illustrates the process of the invention. Those familiar with the art will recognize that modifications and variations of the example may be made in the practice of the invention.

EXAMPLE

Preparation of Propoxy-n-Butyraldehyde

A 100-ml stainless-steel autoclave was charged with 4.06 g (0.07 mol) of allyl alcohol, 2.1 g (0.07 mol) of formaldehyde, 21 g (0.35 mol) of n-propanol, and 100 g (5.0 mols) of hydrogen fluoride. The autoclave was maintained at about −30° C for about 30 minutes. Hydrogen fluoride was distilled from the reaction product and the distillation bottoms were analyzed by vapor-phase chromatography using isobutyl alcohol as a standard.

Conversion of formaldehyde was essentially complete. The crude product contained 4-propoxy-n-butyraldehyde and 4-alloyloxy-n-butyraldehyde in a mol ratio of about 13:1, respectively.

When an equivalent amount of ethanol, methanol, isobutanol and n-butanol is substituted for propanol in the above example, the corresponding 4-alkoxy-n-butyraldehyde is prepared.

What is claimed is:

1. A process for preparing 4-alkoxy-n-butyraldehyde which comprises contacting allyl alcohol, formaldehyde and a $C_1$ to $C_{20}$ primary alcohol in the presence of hydrogen fluoride at a temperature of from about −100° to about 10° C and a pressure of from about 10 to about 1000 psia.

2. A process according to claim 1 wherein the molar ratio of allyl alcohol to formaldehyde to alcohol is from about 1:1:1 to about 1:10:10.

3. A process according to claim 2 wherein the molar ratio of allyl alcohol to formaldehyde to alcohol is from about 1:1:4 to about 1:4:6.

4. A process according to claim 1 wherein the weight ratio of hydrogen fluoride to reactants is from about 1:1 to about 10:1.

5. A process according to claim 4 wherein the weight ratio of hydrogen fluoride to reactants is from about 2:1 to about 5:1.

6. A process according to claim 1 wherein the temperature is from about $-70°$ to about $-10°$ C.

7. A process according to claim 1 wherein the pressure is about 1 atmosphere.

8. A process according to claim 1 wherein the temperature is about $-30°$ C, the pressure is about 1 atmosphere, the allyl alcohol to formaldehyde to a alcohol mol ratio is about 1:1:5 and the weight ratio of hydrogen fluoride to reactants is about 3.7:1.

9. A process according to claim 1 wherein said alcohol is a $C_1$ to $C_{10}$ primary alcohol.

10. A process according to claim 9 wherein said alcohol is selected from the group consisting essentially of methanol, ethanol, propanol, n-butanol, or mixtures thereof.

11. A process according to claim 1 wherein said alcohol is saturated.

* * * * *